(12) United States Patent
Malinski et al.

(10) Patent No.: US 12,043,588 B2
(45) Date of Patent: Jul. 23, 2024

(54) SOLID OXIDE AND CHEMICALLY-TREATED SOLID OXIDE CATALYSTS FOR THE PRODUCTION OF POLYALPHAOLEFINS

(71) Applicant: Chevron Phillips Chemical Company LP, The Woodlands, TX (US)

(72) Inventors: Thomas J. Malinski, Porter, TX (US); Max P. McDaniel, Bartlesville, OK (US); Steven M. Bischof, Spring, TX (US); Graham R. Lief, Bartlesville, OK (US); Holly A. Ramirez, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 18/536,405

(22) Filed: Dec. 12, 2023

(65) Prior Publication Data
US 2024/0199510 A1    Jun. 20, 2024

Related U.S. Application Data

(60) Provisional application No. 63/387,517, filed on Dec. 15, 2022.

(51) Int. Cl.
| | | |
|---|---|---|
| *C07C 2/10* | (2006.01) |
| *B01J 21/04* | (2006.01) |
| *B01J 21/08* | (2006.01) |
| *B01J 21/16* | (2006.01) |
| *B01J 37/02* | (2006.01) |
| *B01J 37/20* | (2006.01) |
| *B01J 37/26* | (2006.01) |

(52) U.S. Cl.
CPC .......... *C07C 2/10* (2013.01); *B01J 21/04* (2013.01); *B01J 21/08* (2013.01); *B01J 21/16* (2013.01); *B01J 37/0215* (2013.01); *B01J 37/20* (2013.01); *B01J 37/26* (2013.01); *C07C 2521/12* (2013.01)

(58) Field of Classification Search
CPC ... B01J 21/04; B01J 21/08; B01J 21/16; B01J 37/0215; B01J 37/20; B01J 37/26; C07C 2/10; C07C 2521/12
See application file for complete search history.

(56) References Cited

U.S. PATENT DOCUMENTS

| | | |
|---|---|---|
| 4,658,078 A | 4/1987 | Slaugh |
| 4,973,788 A | 11/1990 | Lin |
| 5,087,788 A | 2/1992 | Wu |
| 6,479,722 B1 | 11/2002 | De Wet |
| 6,548,724 B2 | 4/2003 | Bagheri |
| 7,129,197 B2 | 10/2006 | Song |
| 8,207,390 B2 | 6/2012 | Wu |
| 8,318,998 B2 | 11/2012 | Crowther |
| 8,426,659 B2 | 4/2013 | Holtcamp |
| 8,455,416 B2 | 6/2013 | Bagheri |
| 8,536,391 B2 | 9/2013 | Small |
| 8,623,974 B2 | 1/2014 | Jiang |
| 8,748,361 B2 | 6/2014 | Wu |
| 8,816,027 B2 | 8/2014 | Crowther |
| 8,841,394 B2 | 9/2014 | Crowther |
| 8,865,959 B2 | 10/2014 | Patil |
| 9,234,150 B2 | 1/2016 | Martin |
| 9,234,151 B2 | 1/2016 | Martin |
| 9,234,152 B2 | 1/2016 | Martin |
| 9,365,788 B2 | 6/2016 | Emett |
| 9,399,746 B2 | 7/2016 | Emett |
| 9,409,834 B2 | 8/2016 | Wu |
| 9,688,792 B2 | 6/2017 | Welle |
| 9,708,549 B2 | 7/2017 | Gee |
| 9,745,230 B2 | 8/2017 | Small |
| 9,796,645 B2 | 10/2017 | Emett |
| 10,005,972 B2 | 6/2018 | Yang |
| 10,336,663 B2 | 7/2019 | Lief |
| 10,435,336 B2 | 10/2019 | Kreischer |
| 10,435,491 B2 | 10/2019 | Bischof |
| 10,654,766 B2 | 5/2020 | Chen |
| 10,919,996 B2 | 2/2021 | McDaniel |
| 10,968,290 B2 | 4/2021 | Crowther |
| 11,021,553 B2 | 6/2021 | Chen |
| 11,028,197 B2 | 6/2021 | Chen |
| 11,078,308 B2 | 8/2021 | Chen |
| 11,078,436 B2 | 8/2021 | Yang |
| 11,084,894 B2 | 8/2021 | Yang |
| 11,186,665 B2 | 11/2021 | Lief |
| 2009/0156874 A1 | 6/2009 | Patil |
| 2013/0253244 A1 | 9/2013 | Emett |
| 2013/0303818 A1 | 11/2013 | Inagaki |
| 2013/0317265 A1 | 11/2013 | Small |
| 2019/0135961 A1 | 5/2019 | Joung |
| 2019/0248936 A1 | 8/2019 | Yang |
| 2019/0359745 A1 | 11/2019 | Chen |
| 2019/0359748 A1 | 11/2019 | Chen |
| 2020/0407657 A1 | 12/2020 | Emett |
| 2021/0122859 A1 | 4/2021 | Rapp |
| 2021/0147661 A1 | 5/2021 | Lief |
| 2021/0395413 A1 | 12/2021 | Lief |

FOREIGN PATENT DOCUMENTS

| | | | |
|---|---|---|---|
| CN | 113150826 B | 11/2023 | |
| EP | 2222823 B1 | 11/2013 | |
| WO | WO-2018013249 A1 * | 1/2018 | ............... C07C 2/06 |

OTHER PUBLICATIONS

International Search Report and Written Opinion issued in corresponding PCT Application No. PCT/US2023/083561, mailed on May 8, 2024. 12 pp.

* cited by examiner

*Primary Examiner* — Brian A McCaig
(74) *Attorney, Agent, or Firm* — Merchant & Gould P.C.

(57) ABSTRACT

Oligomer products are produced by reacting an alpha olefin and a vinylidene compound in the presence of a solid catalyst, such as a solid oxide or a chemically-treated solid oxide. Metallocene compounds, organoaluminum compounds, and $BF_3$ are not needed to perform the reaction. Oligomer products formed by processes disclosed herein have a trimer:tetramer weight ratio of at least 2:1.

35 Claims, No Drawings

SOLID OXIDE AND CHEMICALLY-TREATED SOLID OXIDE CATALYSTS FOR THE PRODUCTION OF POLYALPHAOLEFINS

REFERENCE TO RELATED APPLICATION

This application claims the benefit of U.S. Provisional Patent Application No. 63/387,517, filed on Dec. 15, 2022, the disclosure of which is incorporated herein by reference in its entirety.

FIELD OF THE INVENTION

The present disclosure generally relates to processes for producing polyalphaolefins using solid catalysts comprising a solid oxide or a chemically treated solid oxide.

BACKGROUND OF THE INVENTION

Processes for reacting alpha olefins and vinylidenes conventionally rely on catalyst systems comprising solution-based catalysts such as $BF_3$ or catalyst systems comprising metallocene compounds with associated co-catalysts and activators. Processes employing alternative solid catalyst systems that can efficiently produce oligomers from alpha olefins and vinylidenes in high yield and selectivity would be beneficial. Accordingly, it is to these ends that the present disclosure is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes disclosed herein can comprise (i) contacting an alpha olefin, a vinylidene, and a solid catalyst in a reaction zone, and (ii) forming an oligomer product in the reaction zone. The solid catalyst can comprise a solid oxide and/or a chemically-treated solid oxide. The oligomer product can have a trimer:tetramer weight ratio of at least 2:1, and generally, an amount of the oligomer product can be at least 2 wt. %, based on the total amount of the alpha olefin and the vinylidene. The process can be performed in the substantial absence of $BF_3$, metallocene compounds, organoaluminum compounds, and the like.

In aspects wherein the solid catalyst comprises a solid oxide, the solid oxide can comprise silica-coated alumina. Alternatively, in aspects wherein the solid catalyst comprises a chemically-treated solid oxide, the chemically-treated solid oxide can comprise a fluorided silica-coated alumina or a sulfated alumina.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the examples and detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the processes described herein are contemplated with or without explicit description of the particular combination. Additionally, unless explicitly recited otherwise, any aspect or feature disclosed herein can be combined to describe inventive processes consistent with the present disclosure.

In this disclosure, while processes are described in terms of "comprising" various components or steps, the processes also can "consist essentially of" or "consist of" the various components or steps, unless stated otherwise.

The terms "a," "an," and "the" are intended to include plural alternatives, e.g., at least one. For instance, the disclosure of "a catalyst" is meant to encompass one catalyst, or mixtures or combinations of more than one catalyst, unless otherwise specified.

The terms "contacting" and "combining" are used herein to describe compositions and processes in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique. Herein, "contacting" or "combining" two or more components can result in a reaction product, such as an oligomer product.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens for Group 17 elements.

The term "hydrocarbon" refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "alkane" refers to a saturated hydrocarbon compound.

The term "olefin" refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono,"

"di," "tri," etc., within the name of the olefin. The olefins can be further identified by the position of the carbon-carbon double bond(s).

The term "alpha olefin" as used herein refers to any olefin that has 1) a carbon-carbon double bond between the first and second carbon atom of the longest contiguous chain of carbon atoms, and 2) at least one hydrogen atom bound to the second carbon of the chain. The term "alpha olefin" includes linear and branched alpha olefins and alpha olefins which can have more than one non-aromatic carbon-carbon double bond, unless expressly stated otherwise. In the case of branched olefins, a branch can be at the 2-position of a 1-alkene (a vinylidene) with respect to the olefin double bond.

Thus, the term "vinylidene" refers to a 1-alkene having an alkyl branch at the 2-position with respect to the olefin double bond. The term "normal alpha olefin" refers to a linear aliphatic hydrocarbon mono-olefin having 1) a carbon-carbon double bond between the first and second carbon atoms, and 2) at least one hydrogen atom bound to the second carbon of the chain. The term "linear internal olefin" refers to a linear aliphatic hydrocarbon mono-olefin having a double bond that is not between the first and second carbon atoms.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Several types of ranges are disclosed herein. When a range of any type is disclosed or claimed, the intent is to disclose or claim individually each possible number that such a range could reasonably encompass, including end points of the range as well as any sub-ranges and combinations of sub-ranges encompassed therein. For example, the molar ratio of alpha olefin and vinylidene in the reaction zone can fall within a range from 5:1 to 1:5. By a disclosure that the molar ratio of alpha olefin and vinylidene in the reaction zone can range from 5:1 to 1:5, the intent is to recite that the molar ratio can be any ratio within the range and, for example, can include any range or combination of ranges from 5:1 to 1:5, such as from 4:1 to 1:4, from 3:1 to 1:3, from 2:1 to 1:2, from 1.5:1 to 1:1.5, or from 1.2:1 to 1:1.2, and so forth. Likewise, all other ranges disclosed herein should be interpreted in a manner similar to this example.

In general, an amount, size, formulation, parameter, range, or other quantity or characteristic is "about" or "approximate," whether or not it is expressly stated to be such. Whether or not modified by the term "about" or "approximately," the claims include equivalents to the quantities or characteristics.

All disclosed product yields are based on the limiting reactant in the respective reaction, unless explicitly stated otherwise. For example, the limiting reactant in a process comprising contacting an alpha olefin and a vinylidene can be either the alpha olefin or the vinylidene when present in a 1:1 molar ratio. In aspects where there is a molar excess of the alpha olefin, the vinylidene would be considered the limiting reagent. Alternatively, in aspects where the vinylidene is provided in molar excess relative to the alpha olefin, the alpha olefin would be considered the limiting reactant.

Oligomer products of the reaction of alpha olefin and vinylidene as referred to herein can include dimers, trimers, and tetramers, where tetramers also may generally include heavier components. Within the context of this disclosure, it will be understood that references to "dimer" within the oligomer product refers to the reaction product of two alpha olefin molecules. Similarly, references to "trimer" within the oligomer product refers to the cross-product of alpha olefin and vinylidene molecules, whereas "tetramer" refers to the reaction product of two vinylidene molecules. Applying this nomenclature to a reaction of 1-decene as the alpha olefin and a $C_{20}$ vinylidene dimer of 1-decene, the dimer in the oligomer product mixture refers to the $C_{20}$ product formed by reaction of two molecules of 1-decene, trimer refers to the $C_{30}$ product formed by reaction of 1-decene and $C_{20}$ vinylidene, and tetramer refers to the $C_{40}$ product formed by reaction of two molecules of $C_{20}$ vinylidene (and also includes $C_{40}$ produced by $C_{20}$ vinylidene and two molecules of 1-decene (if any) and $C_{40}$ produced by $C_{30}$ trimer and 1-decene (if any)).

Although any methods, devices, and materials similar or equivalent to those described herein can be used in the practice or testing of the disclosure, the typical methods, devices, and materials are herein described.

All publications and patents mentioned herein are incorporated by reference in their entirety for the purpose of describing and disclosing, for example, the constructs and methodologies that are described in the publications and patents, which might be used in connection with the present disclosure.

DETAILED DESCRIPTION OF THE INVENTION

Disclosed herein are solid catalysts and processes employing the solid catalysts to catalyze the reaction of an alpha olefin and a vinylidene to form an oligomer product. Solid catalysts can comprise solid oxides and chemically treated solid oxides. Unexpectedly, the solid catalysts disclosed herein can be suitable replacements for solution-based catalysts (e.g., $BF_3$-catalyzed oligomerizations) and without the need for metallocene compounds and organoaluminum compounds.

Solid Catalysts

Solid catalysts described herein generally can refer to solid oxides and chemically-treated solid oxides or like material as disclosed, for instance, in U.S. Pat. Nos. 8,536,391 and 10,919,996. In certain aspects, the solid oxide can comprise oxygen and at least one element selected from Group 2, 3, 4, 5, 6, 7, 8, 9, 10, 11, 12, 13, 14, or 15 of the periodic table, or comprise oxygen and at least one element selected from the lanthanide or actinide elements; alternatively, the solid oxide can comprise oxygen and at least one element selected from Group 4, 5, 6, 12, 13, or 14 of the periodic table, or comprise oxygen and at least one element selected from the lanthanide elements. (See: Hawley's Condensed Chemical Dictionary, 11th Ed., John Wiley & Sons; 1995; Cotton, F. A.; Wilkinson, G.; Murillo; C. A.; and Bochmann; M. Advanced Inorganic Chemistry, 6th Ed., Wiley-Interscience, 1999.) In some aspects, the inorganic oxide can comprise oxygen and at least one element selected from Al, B, Be, Bi, Cd, Co, Cr, Cu, Fe, Ga, La, Mn, Mo, Ni, Sb, Si, Sn, Sr, Th, Ti, V, W, P, Y, Zn or Zr; alternatively, the inorganic oxide can comprise oxygen and at least one element selected from Al, B, Si, Ti, P, Zn or Zr.

In an aspect, the solid oxide can comprise $Al_2O_3$, $B_2O_3$, BeO, $Bi_2O_3$, CdO, $CO_3O_4$, $Cr_2O_3$, CuO, $Fe_2O_3$, $Ga_2O_3$, La2O3, $Mn_2O_3$, $Mo_3$, NiO, $P_2O_5$, $Sb_2O$ s, $SiO_2$, $SnO_2$, SrO, $ThO_2$, $TiO_2$, $WO_3$, $Y_2O_3$, ZnO, $ZrO_2$, mixed oxides thereof, and combinations thereof. In certain aspects, the solid oxide can comprise silica, alumina, silica-alumina, silica-coated alumina, aluminum phosphate, aluminophosphate, heteropolytungstate, titania, zirconia, magnesia, boria, zinc oxide, a mixed oxide thereof, or any combination thereof. In other aspects, the solid oxide can comprise silica-coated alumina.

The silica content of the silica-coated alumina, while not being necessarily limited to, often ranges from 10 to 80 wt. %, based on the weight of the silica-coated alumina. More often, the silica-coated alumina contains from 20 to 60 wt. % silica in one aspect, from 25 to 55 wt. % silica in another aspect, and from 35 to 45 wt. % silica in yet another aspect. These percentages are based on the weight of silica-coated alumina.

Alternatively, or additionally, solid catalysts can comprise chemically-treated solid oxides. In one aspect and any aspect of this disclosure, the solid catalyst can comprise a chemically-treated solid oxide comprising a solid oxide treated with at least one electron-withdrawing anion, wherein the solid oxide can comprise any oxide that is characterized by a high surface area, and the electron-withdrawing anion can comprise any anion that increases the acidity of the solid oxide as compared to the solid oxide that is not treated with at least one electron-withdrawing anion.

The solid oxide material can be treated with a source of halide ion, sulfate ion, or a combination thereof. In one aspect, the solid oxide material can be treated with a source of sulfate (termed a sulfating agent), a source of phosphate (termed a phosphating agent), a source of iodide ion (termed an iodiding agent), a source of bromide ion (termed a bromiding agent), a source of chloride ion (termed a chloriding agent), a source of fluoride ion (termed a fluoriding agent), or any combination thereof, and calcined to provide the chemically-treated solid oxide.

In certain aspects, the solid catalyst can comprise a chemically-treated solid oxide comprising a solid oxide treated with an electron-withdrawing anion, wherein the solid oxide is selected from silica, alumina, silica-alumina, silica-coated alumina, aluminum phosphate, heteropolytungstates, titania, zirconia, magnesia, boria, zinc oxide, mixed oxides thereof, or mixtures thereof, and the electron-withdrawing anion is selected from fluoride, chloride, bromide, phosphate, triflate, bisulfate, sulfate, fluorophosphate, fluorosulfate, or any combination thereof. Thus, in certain aspects wherein the solid catalyst comprises a chemically-treated solid oxide, the chemically-treated solid oxide can comprise fluorided alumina, chlorided alumina, bromided alumina, sulfated alumina, phosphated alumina, fluorided silica-alumina, chlorided silica-alumina, bromided silica-alumina, sulfated silica-alumina, phosphated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof. In certain aspects, the chemically-treated solid oxide can comprise sulfated alumina and/or fluorided silica-coated alumina.

While not being limited thereto, the electron-withdrawing anion content (e.g., fluorine or sulfate) of the chemically-treated solid oxide can range from 1 to 25 wt. %. In many instances, the fluorided silica-coated alumina described herein can contain from 1 to 15 wt. % F, such as from 2 to 10 wt. % F, or from 3 to 7 wt. % F, and the like. These weight percentages are based on the weight of the fluorided silica-coated alumina. Analogously, the sulfated alumina described herein often can contain from 1 to 30 wt. % sulfate, such as from 5 to 25 wt. % sulfate, or from 10 to 25 wt. % sulfate, and the like. These weight percentages are based on the weight of the sulfated alumina.

The solid oxide can be calcined or uncalcined; alternatively, calcined; or alternatively, uncalcined. In aspects where the solid catalyst is a chemically-treated solid oxide, the solid oxide can be calcined prior to, during, or after the solid oxide compound is contacted with the electron-withdrawing anion source. Calcining of the solid oxide or treated solid oxide is generally conducted in an ambient atmosphere; alternatively, in a dry ambient atmosphere. The solid oxide or chemically-treated solid oxide can be calcined at a temperature from 200° C. to 900° C.; alternatively, from 300° C. to 800° C.; alternatively, from 400° C. to 700° C.; or alternatively, from 350° C. to 550° C. The period of time at which the solid oxide or chemically-treated solid oxide is maintained at the calcining temperature can be 1 minute to 100 hours; alternatively, from 1 hour to 50 hours; alternatively, from 3 hours to 20 hours; or alternatively, from 1 to 10 hours.

Pore characteristics for the solid catalysts disclosed herein can affect the yield of the oligomer product and the trimer selectivity. In certain aspects, the solid oxide or chemically-treated solid oxide can have a pore volume greater than or equal to 0.1 mL/g, or greater than or equal to 0.5 mL/g. In other aspects, the pore volume can be greater than or equal to 0.8 mL/g, or greater than or equal to 1 mL/g. In another aspect, the pore volume can be greater than or equal to 1.2 yet another aspect, the pore volume can be in a range from 0.5 mL/g to 1.8 mL/g, such as, for example, from 0.8 mL/g to 1.7 mL/g, or from 1 mL/g to 1.6 mL/g.

The solid catalysts disclosed herein also can be characterized by a surface area in a range from 100 to 1000 $m^2/g$, from 150 to 750 $m^2/g$, or from 200 to 600 $m^2/g$. The surface area of the solid catalyst can range from 250 to 500 $m^2/g$ in another aspect of this invention. Solid catalysts having surface areas greater than 300 $m^2/g$, greater than 350 $m^2/g$, greater than 400 $m^2/g$, or greater than 450 $m^2/g$, can be employed in aspects of this invention.

Oligomerization Processes

Processes disclosed herein can comprise contacting an alpha olefin, a vinylidene, and a solid catalyst in a reaction zone, and forming an oligomer product in the reaction zone. In certain aspects, the solid catalyst can comprise a solid oxide or a chemically-treated solid oxide, for example those described above. Unexpectedly, these processes—utilizing a solid catalyst—form the oligomer product in a high yield and with excellent trimer selectivity, in the substantial absence of conventional oligomerization catalysts including metallocenes and $BF_3$.

A wide range of alpha olefin monomers can be reacted in the processes provided herein. For example, the alpha olefin can comprise, consist essentially of, or consist of, a $C_4$ to $C_{30}$ alpha olefin; alternatively, a $C_4$ to $C_{18}$ alpha olefin; alternatively, a $C_4$ to $C_{16}$ alpha olefin; alternatively, a $C_5$ to $C_{18}$ alpha olefin; alternatively, a $C_6$ to $C_{16}$ alpha olefin; or alternatively, a $C_8$ to $C_{12}$ alpha olefin. In an aspect, the oligomer product can be produced from an alpha olefin comprising, consisting essentially of, or consisting of, a $C_6$ alpha olefin, a $C_8$ alpha olefin, a $C_{10}$ alpha olefin, a $C_{12}$ alpha olefin, a $C_{14}$ alpha olefin, a $C_{16}$ alpha olefin, or any combination thereof; alternatively, a $C_8$ alpha olefin, a $C_{10}$ alpha olefin, a $C_{12}$ alpha olefin, or any combination thereof; alternatively, a $C_6$ alpha olefin; alternatively, a $C_8$ alpha olefin; alternatively, a $C_{10}$ alpha olefin; alternatively, a $C_{12}$ alpha olefin; alternatively, a $C_{14}$ alpha olefin; alternatively, a $C_{16}$ alpha olefin; or alternatively, a $C_{18}$ alpha olefin. In a further aspect, the alpha olefin can comprise, consist essentially of, or consist of 1-butene, 1-pentene, 1-hexene, 1-octene, 1-decene, 1-dodecene, 1-tetradecene, 1-hexadecene, or any combination thereof. For instance, the alpha olefin can comprise, consist essentially of, or consist of 1-octene; alternatively, 1-decene; or alternatively, 1-dodecene.

The alpha olefin monomers can be derived from ethylene that is produced from fossil-based feedstocks, bio-based feedstocks, or recycled, circular feedstocks that are fossil-based or bio-based. For example, the alpha olefin can be derived from ethylene that is produced from natural gas feedstocks. Alternatively, the alpha olefin can be derived from ethylene produced from naphtha obtained from crude oil. Alternatively, the alpha olefin can be derived from ethylene produced from ethanol, wherein the ethanol is derived from cellulosic or lignocellulosic feedstocks (i.e., sugar cane, corn, etc.). Alternatively, the alpha olefin can be derived from ethylene produced from recycled plastic materials that have been pyrolyzed to form a circular pyrolysis gas or pyrolysis oil feedstock. When a renewable or circular feedstock is used, the resulting products can be certified as circular or renewable products. Any suitable amount of the alpha olefin feed can be a normal alpha olefin. Generally, the alpha olefin contains at least 50 wt. % normal alpha olefin(s), and more often, contains at least 60 wt. %, at least 70 wt. %, at least 80 wt. %, at least 85 wt. %, at least 90 wt. %, at least 92.5 wt. %, or at least 95 wt. % of normal alpha olefin(s), and in some aspects, less than or equal to 99.9 wt. %, less than or equal to 99.5 wt. %, less than or equal to 97 wt. %, or less than or equal to 95 wt. % of normal alpha olefin(s), and in other aspects, a range from any minimum amount disclosed herein to any maximum amount disclosed herein of normal alpha olefin(s), e.g., the alpha olefin contains from 85 wt. % to 95 wt. % or from 90 wt. % to 99 wt. %, of 1-hexene, 1-octene, 1-decene, 1-dodecene, or 1-tetradecene. Thus, mixtures of various alpha olefins (or normal alpha olefins) having different numbers of carbon atoms can be used, or alpha olefins (or normal alpha olefins) having predominantly a single number of carbon atoms can be used. While a mixture of different carbon number olefins can be utilized, the processes disclosed herein are particularly well suited for use with alpha olefins (or normal alpha olefins) having a single carbon number.

In an aspect, the alpha olefin monomer can be a $C_{10}$ mono-olefin mixture comprising 2-butyl-1-hexene, 3-propyl-1-heptene, 4-ethyl-1-octene, 5-methyl-1-nonene, or any combination thereof. In an aspect, the alpha olefin monomer can also contain $C_{14}$ mono-olefins. In a further aspect, an alpha olefin feed suitable for use in the processes described herein is described in U.S. Pat. No. 10,435,336.

Vinylidenes suitable for use in the processes described herein generally can comprise a 1-alkene branched at the 2-position as defined above. In certain aspects, vinylidene compounds can have a formula $CH_2=CR_1R_2$, wherein $R_1$ and $R_2$ independently are a substituted or unsubstituted hydrocarbyl or alkyl substituent (e.g., a $C_2$-$C_{32}$ hydrocarbyl or alkyl, a $C_2$-$C_{24}$ hydrocarbyl or alkyl, a $C_2$-$C_{16}$ hydrocarbyl or alkyl, a $C_4$-$C_{16}$ hydrocarbon or alkyl, or a $C_4$-$C_{12}$ hydrocarbyl or alkyl). Taking $R_1$ and $R_2$ together with the double bond carbons, the vinylidene compound can comprise, in certain aspects, a $C_8$-$C_{32}$ olefin, a $C_8$-$C_{24}$ olefin, a $C_{12}$-$C_{28}$ olefin, a $C_{16}$-$C_{24}$ olefin, a $C_{20}$ olefin, or any combination thereof. In certain aspects, the vinylidene compound can be the dimer of an alpha olefin, for instance the dimer product formed in an alpha olefin oligomerization process. Thus, the vinylidene can comprise, for instance, a dimer of 1-butene, a dimer of 1-pentene, a dimer of 1-hexene, a dimer of 1-octene, a dimer of 1-decene, a dimer of 1-dodecene, a dimer of 1-tetradecene, a dimer of 1-hexadecene, or any combination thereof. In certain aspects, the vinylidene can comprise a dimer of 1-decene.

Relative amounts of the alpha olefin and vinylidene in the reaction zone can affect the relative amounts of individual oligomers formed within the resulting oligomer product. For instance, a "dimer" may be formed in the oligomer product by the reaction of two molecules of the alpha olefin. Without being bound by theory, an excess amount of alpha olefin in the reaction zone relative to vinylidene may cause a relative increase in the dimer reaction product pathway. Alternatively, balancing the molar ratio of the alpha olefin and vinylidene may prioritize a "trimer" product, formed as the cross-product of the alpha olefin and vinylidene, and minimizing the self-reaction of either the alpha olefin or the vinylidene. While not limited thereto, the molar ratio of the alpha olefin to the vinylidene in the reaction zone can range from 5:1 to 1:5, such as from 4:1 to 1:4, from 3:1 to 1:3, from 2:1 to 1:2, from 1.5:1 to 1:1.5, or from 1.2:1 to 1:1.2. For instance, a molar ratio of approximately 1:1 can be utilized the step (i) of the process.

Surprisingly, the oligomer product can be obtained in the presence of the solid catalyst even under relatively mild reaction conditions. The amount of the solid catalyst in the reaction zone, based on the total amount of the alpha olefin and the vinylidene, often can range from 2 wt. % to 50 wt. %, from 2 wt. % to 20 wt. %, from 5 wt. % to 15 wt. %, or from 7 to 13 wt. %, although not limited thereto. In certain aspects either or both of the contacting step and the forming step can be conducted at standard conditions, e.g., a temperature in a range from 20° C. to 30° C. and atmospheric pressure. Alternatively, step (i) and step (ii) independently can be conducted at a temperature in a range from 0° C. to 100° C., from 10° C. to 60° C., or from 20° C. to 40° C. The duration of the step to form the oligomer product is not limited to any particular length of time, and generally may be completed within any period of time suitable for the reaction process. In certain aspects, the oligomer product may be formed under any conditions described above in less than 8 hr, less than 5 hr, less than 2 hr, less than 1 hr, or less than 15 min. In other aspects, the duration of forming the oligomer product can be in a range from 1 min to 10 hr, from 5 min to 3 hr, from 15 min to 2 hr, or from 30 min to 90 min.

Under any conditions described above, processes disclosed herein can result in a conversion of a limiting reagent to the oligomerization process (e.g., alpha olefin and/or vinylidene) of at least 2 wt. %, at least 5 wt. %, at least 10 wt. %, at least 20 wt. %, or at least 40 wt. %. Alternatively, the conversion of the alpha olefin and/or the vinylidene can be in a range from 2 wt. % to 50 wt. %, from 5 wt. % to 50 wt. %, or from 10 wt. % to 25 wt. %. In certain aspects, a yield of the oligomer product obtained by the process in the product mixture can be at least 2 wt. %, at least 5 wt. %, at least from 2 wt. % to 50 wt. %, or from 5 wt. % to 40 wt. %, based on a total amount of the alpha olefin and the vinylidene.

The oligomer product formed by processes disclosed herein also may be characterized by the relative amount of specific oligomer products formed in the product mixture. For instance, it can be desirable to maximize the amount of trimer (i.e., the cross product of the alpha olefin and vinylidene) produced in the process and present in the oligomer product. The oligomer selectivity can be driven by catalyst selection and so any catalyst employed must be able to achieve or preserve a desirable oligomer product profile. Surprisingly, processes disclosed herein that employ solid catalysts are able to produce trimer in much greater amounts than other alternative oligomer products, even in the substantial absence of $BF_3$, metallocene compounds, organoaluminum compounds, and the like. In certain aspects, ratio of trimer:tetramer weight ratio in the oligomer product can be in a range from 2:1 to 20:1, from 2:1 to 15:1, from 3:1 to 10:1, or from 2:1 to 6:1.

Oligomerization processes disclosed herein can exclude $BF_3$, metallocene compounds, organoaluminum compounds (including aluminoxanes), or any combination thereof from the reaction mixture. Thus, aspects disclosed herein are contemplated as being substantially free of metallocene compounds (i.e., no more than 10 ppm by weight relative to the amount of alpha olefin and vinylidene), substantially free of $BF_3$ (i.e., no more than 1 ppm by weight relative to the amount of alpha olefin and vinylidene), and/or substantially free of organoaluminum compounds (i.e., no more than 1 ppm by weight relative to the amount of alpha olefin and vinylidene). In an aspect, the amount of metallocene present in the reaction zone relative to the amount of alpha olefin and vinylidene can be less than 100 ppm, less than 10 ppm, less than 1 ppm, or less than 0.1 ppm, or less than 1 ppb (by weight). Additionally or alternatively, the amount of $BF_3$ present in the reaction zone relative to the amount of alpha olefin and vinylidene can be less than 2.0 wt. %, less than 1.0 wt. %, less than 0.1 wt. %, less than 0.01 wt. %, less than 10 ppm, less than 1 ppm, or less than 0.1 ppm (by weight). Additionally or alternatively, the amount of organoaluminum compounds present in the reaction zone relative to the amount of alpha olefin and vinylidene can be less than 100 ppm, less than 10 ppm, less than 1 ppm, less than 0.1 ppm, or less than 1 ppb.

Taken together, it will be understood that the processes disclosed herein can comprise a solid catalyst without introducing catalyst components that may be difficult to separate from the oligomer product in downstream processing. In certain aspects, the processes can further comprise a step of separating the solid catalyst from the oligomer product, and unlike chemical separation methods, beneficially a filtration step or other suitable separation technique can be used to efficiently remove and/or recycle the solid catalyst from the oligomer product. The oligomer product, after being discharged from the reaction zone, can be isolated, such as by separating unreacted alpha olefin and vinylidene. The desired oligomer product can be subject to distillation or fractionation to separate or isolate the dimer, trimer, tetramer, etc., components of the oligomer product. The oligomer product, or any portion thereof (e.g., trimer), or a mixture thereof, can be hydrogenated to form a polyalphaolefin (PAO).

EXAMPLES

The disclosure is further illustrated by the following examples, which are not to be construed in any way as imposing limitations to the scope of this disclosure. Various other aspects, modifications, and equivalents thereof, which after reading the description herein, can suggest themselves to one of ordinary skill in the art without departing from the spirit of the present disclosure or the scope of the appended claims. These examples demonstrate that reaction between vinylidene compounds and alpha olefins can be effectively catalyzed in high yield and specificity by solid catalysts disclosed herein, in the substantial absence of $BF_3$, the substantial absence of a metallocene compound, and the substantial absence of an organoaluminum compounds.

Examples 1-9

$C_{20}$ vinylidene was obtained as the fractionated dimer product of metallocene-catalyzed reaction of 1-decene. In a representative example, a 1 gallon batch reactor was charged with 1-decene (1350 g). A syringe was charged with MAO (16 mL, 10 wt. % solution in toluene) and [η-1-(2,3,4,5,6-pentafluorophenyl)indenyl][$η^5$-cyclopentadienyl]zirconium dichloride (27.0 mg). The catalyst mixture was shaken to mix and was then charged to the reactor under a nitrogen purge. The reactor was heated to 90° C. while stirring at 600-900 rpm. Once the reactor temperature had reached setpoint, hydrogen was charged to the reactor in four equivalent charges of 126 mg at time 0, 15, 30, and 45 minutes. After 60 minutes, the reactor was cooled to 35° C. A solution of 10% HCL in isopropyl alcohol (10 mL total charge) was added and the reactor contents were removed. The oligomer product was filtered through celite yielding a clear-colorless liquid. The reaction mixture was then distilled to separate the $C_{20}$ vinylidene from unreacted monomer and $C_{30}$+ material.

Generally, the $C_{20}$ vinylidene herein (95+ wt. % purity) was mixed for 1 hr with 1-decene in a 1:1 molar ratio in the presence of 10 wt. % of a solid catalyst at approximately 25° C. The reaction mixture was then filtered and analyzed by gas chromatography to determine the yield of oligomer product formed in the reaction mixture, and to determine the relative amount of certain oligomers within the oligomer product (e.g., the trimer:tetramer weight ratio). Examples 1-9 were conducted to examine the effect of certain solid catalysts and alternate preparations and attributes of the solid catalysts on the oligomer yield and trimer:tetramer weight ratio.

Gas chromatographic (GC) analyses were performed using a split injection method on an Agilent Technologies 7890B gas chromatograph with a flame ionization detector (FID). Initial oven temperature was 40° C. for 7 minutes and increased 20° C./min to 430° C. and held for 20 minutes. The column was an all-purpose capillary column (Agilent CP7542 CP-SimDist UltiMetal, 10 m×0.53 mm×0.17 μm). Data analysis was performed using Chemstation software.

In the following examples, various oxide supports or carriers were treated and calcined as indicated in the Table I below. In Example 1, an alumina was obtained from W.R. Grace having a surface area of about 300 m²/g, a pore volume of about 1.2 mL/g, and an average particle size of about 100 microns. A sample of this alumina was first calcined briefly at 600° C., then it was impregnated with an aqueous solution of sulfuric acid to incipient wetness, so that after drying the support contain 15 wt. % $H_2SO_4$. A final calcining treatment was performed for three hours at 600° C., followed by purging in nitrogen and storage for later use. In Example 2, the same alumina was treated with phosphoric acid in a similar treatment. The final product contained a phosphorous to aluminum molar ratio of 0.2:1. In Example 3, a silica-coated alumina containing 40% silica was used, having a surface area of about 450 m$^2$/g and a pore volume of 1.1 mL/g. It was impregnated to incipient wetness with an aqueous solution of tetrafluoroboric acid, and then dried and calcined for three hours at 600° C. The final product contained about 4 wt. % F. In example 4, a silica was obtained from W.R. Grace having a surface area of 500 m$^2$/g surface area, a pore volume of 1.5 mL/g, and an average particle size of 100 microns. This support was given a similar treatment as described in Example 3. In Example 5, the silica-coated alumina used above was calcined at 600° C. for 3 hours. Example 6 used the same procedure as that in Example 3 except that the final calcination treatment was at 400° C. Example 7 used the same procedure as that described in Example 1, except that 50% more sulfuric acid was impregnated and the final calcination temperature was 400° C. Example 8 used an acid-leached bentonite sold commercially as F-30×, calcined at 300° C. Example 9 used the same protocol as that described in Example 3 except that the support had a pore volume of 1.5 mL/g.

The solid catalysts of Examples 1-9, the oligomer yield, and the trimer:tetramer weight ratio in the oligomer product are summarized in Table I. Unexpectedly, with the exception of Example 2 and Example 4, the solid catalysts were able to produce significant amounts of oligomer product. Oligomer yields for Examples 1 and 5-9 ranged from 8 to 33 wt. %. Interestingly, the silica-coated alumina solid catalyst of Example 5 had the highest oligomer product yield. Trimer to tetramer weight ratios were at least 2:1 and surprisingly approached 10:1. The solid catalysts of Examples 3 and 5-6 resulted in unexpectedly high trimer:tetramer weight ratios in the 5:1 to 9:1 range.

TABLE I

Summary of Examples 1-9.

| Example | Solid Catalyst | Oligomer Yield (wt. %) | Trimer to Tetramer Ratio |
| --- | --- | --- | --- |
| 1 | Sulfated alumina | 11 | 3.2 |
| 2 | Phosphated alumina | 0 | N/A |
| 3 | Fluorided silica-coated alumina | 2 | 8.6 |
| 4 | Fluorided silica | 0 | N/A |
| 5 | Silica-coated alumina | 33 | 5.1 |
| 6 | Fluorided silica-coated alumina | 8 | 5.1 |
| 7 | Sulfated alumina | 16 | 3.2 |
| 8 | Sulfated bentonite | 13 | 2.2 |
| 9 | Fluorided silica-coated alumina | 25 | 2.8 |

The disclosure is described above with reference to numerous aspects and specific examples. Many variations will suggest themselves to those skilled in the art in light of the above detailed description. All such obvious variations are within the full intended scope of the appended claims. Other aspects of the disclosure can include, but are not limited to, the following (aspects are described as "comprising" but, alternatively, can "consist essentially of" or "consist of"):

Aspect 1. A process comprising:
(i) contacting an alpha olefin, a vinylidene, and a solid catalyst in a reaction zone, wherein the solid catalyst comprises a solid oxide and/or a chemically-treated solid oxide; and
(ii) forming an oligomer product in the reaction zone having a trimer:tetramer ratio of at least 2:1.

Aspect 2. The process of aspect 1, wherein the solid catalyst comprises the solid oxide, and the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or any combination thereof.

Aspect 3. The process of aspect 1, wherein the solid catalyst comprises the solid oxide, and the solid oxide comprises silica-coated alumina.

Aspect 4. The process of aspect 1, wherein the solid catalyst comprises the chemically-treated solid oxide, and the chemically-treated solid oxide comprises fluorided alumina, chlorided alumina, bromided alumina, sulfated alumina, phosphated alumina, fluorided silica-alumina, chlorided silica-alumina, bromided silica-alumina, sulfated silica-alumina, phosphated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof.

Aspect 5. The process of aspect 1, wherein the solid catalyst comprises the chemically-treated solid oxide, and the chemically-treated solid oxide comprises a sulfated solid oxide and/or a fluorided solid oxide.

Aspect 6. The process of aspect 1, wherein the solid catalyst comprises the chemically-treated solid oxide, and the chemically-treated solid oxide comprises sulfated alumina and/or fluorided silica-coated alumina.

Aspect 7. The process of any one of the preceding aspects, wherein the solid catalyst has any suitable pore volume (e.g., from 0.5 mL/g to 1.8 mL/g) and any suitable BET surface area (e.g., from 100 to 1000 m$^2$/g).

Aspect 8. The process of any one of the preceding aspects, wherein the alpha olefin comprises any suitable alpha olefin, e.g., a $C_4$-$C_{30}$ alpha olefin, a $C_4$-$C_{18}$ alpha olefin, or a $C_6$-$C_{14}$ alpha olefin.

Aspect 9. The process of any one of the preceding aspects, wherein the alpha olefin comprises 1-butene, 1-pentene, 1-hexene, 1-octene, 1-decene, 1-dodecene, 1-tetradecene, 1-hexadecene, or any combination thereof.

Aspect 10. The process of any one of the preceding aspects, wherein the alpha olefin comprises 1-decene.

Aspect 11. The process of any one of the preceding aspects, wherein the vinylidene comprises any suitable vinylidene, e.g., a $C_8$-$C_{32}$ vinylidene or a $C_{12}$-$C_{28}$ vinylidene.

Aspect 12. The process of any one of the preceding aspects, wherein the vinylidene comprises a dimer of 1-butene, a dimer of 1-pentene, a dimer of 1-hexene, a dimer of 1-octene, a dimer of 1-decene, a dimer of 1-dodecene, a dimer of 1-tetradecene, a dimer of 1-hexadecene, or any combination thereof.

Aspect 13. The process of any one of the preceding aspects, wherein the vinylidene comprises a dimer of 1-decene.

Aspect 14. The process of any one of the preceding aspects, wherein a molar ratio of the alpha olefin to the vinylidene is in any suitable range, e.g., from 2:1 to 1:2, from 1.5:1 to 1:1.5, or from 1.2:1 to 1:1.2.

Aspect 15. The process of any one of the preceding aspects, wherein an amount of the solid catalyst in the reaction zone is in any suitable range, e.g., from 2 wt. % to 20 wt. %, from 5 wt. % to 15 wt. %, or from 7 wt. % to 13 wt. %, based on the total amount of alpha olefin and vinylidene.

Aspect 16. The process of any one of the preceding aspects, wherein step (i) and step (ii) are conducted independently at any suitable temperature, e.g., from 0° C. to 100° C., from 10° C. to 60° C., or from 20° C. to 40° C.

Aspect 17. The process of any one of the preceding aspects, wherein the oligomer product is formed in any suitable time period, e.g., from 5 min to 3 hr, from 15 min to 2 hr, or from 30 min to 90 min.

Aspect 18. The process of any one of the preceding aspects, wherein the reaction zone is substantially free of $BF_3$.

Aspect 19. The process of any one of the preceding aspects, wherein the reaction zone is substantially free of metallocene compounds.

Aspect 20. The process of any one of the preceding aspects, wherein the reaction zone is substantially free of organoaluminum compounds.

Aspect 21. The process of any one of the preceding aspects, wherein the oligomer product has any suitable weight ratio of trimer:tetramer, e.g., from 2:1 to 15:1, from 3:1 to 10:1, or from 2:1 to 6:1.

Aspect 22. The process of any one of the preceding aspects, wherein the process has any suitable conversion of the vinylidene, e.g., at least 2 wt. %, from 5 wt. % to 50 wt. %, or from 10 wt. % to 25 wt. %.

Aspect 23. The process of any one of the preceding aspects, wherein a yield of the oligomer product is in any suitable range, e.g., at least 2 wt. %, from 2 wt. % to 50 wt. %, or from 5 wt. % to 40 wt. %, based on a total amount of the alpha olefin and the vinylidene.

Aspect 24. The process of any one of the preceding aspects, further comprising a step of separating the solid catalyst from the oligomer product.

Aspect 25. The process of any one of the preceding aspects, further comprising a step of isolating the oligomer product discharged from the reaction zone.

Aspect 26. The process of any one of the preceding aspects, further comprising a step of hydrogenating the oligomer product to form a polyalphaolefin (PAO).

We claim:

1. A process comprising:
   (i) contacting an alpha olefin, a vinylidene, and a solid catalyst in a reaction zone, wherein the solid catalyst comprises a solid oxide and/or a chemically-treated solid oxide and the reaction zone is substantially free of $BF_3$, metallocene compounds, and organoaluminum compounds; and
   (ii) forming an oligomer product in the reaction zone having a trimer:tetramer weight ratio of at least 2:1.

2. The process of claim 1, wherein the solid catalyst comprises the solid oxide, and the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or any combination thereof.

3. The process of claim 1, wherein the solid catalyst comprises the solid oxide, and the solid oxide comprises silica-coated alumina.

4. The process of claim 1, wherein the solid catalyst comprises the chemically-treated solid oxide, and the chemically-treated solid oxide comprises fluorided alumina, chlorided alumina, bromided alumina, sulfated alumina, phosphated alumina, fluorided silica-alumina, chlorided silica-alumina, bromided silica-alumina, sulfated silica-alumina, phosphated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof.

5. The process of claim 1, wherein the solid catalyst comprises the chemically-treated solid oxide, and the chemically-treated solid oxide comprises sulfated alumina and/or fluorided silica-coated alumina.

6. The process of claim 1, wherein the alpha olefin comprises a $C_4$-$C_{30}$ alpha olefin.

7. The process of claim 1, wherein the alpha olefin comprises 1-butene, 1-pentene, 1-hexene, 1-octene, 1-decene, 1-dodecene, 1-tetradecene, 1-hexadecene, or any combination thereof.

8. The process of claim 1, wherein the alpha olefin comprises 1-decene.

9. The process of claim 1, wherein the vinylidene comprises a dimer of 1-butene, a dimer of 1-pentene, a dimer of 1-hexene, a dimer of 1-octene, a dimer of 1-decene, a dimer of 1-dodecene, a dimer of 1-tetradecene, a dimer of 1-hexadecene, or any combination thereof.

10. The process of claim 1, wherein the vinylidene comprises a dimer of 1-decene.

11. The process of claim 1, wherein a molar ratio of the alpha olefin to the vinylidene is in a range from 2:1 to 1:2.

12. The process of claim 1, wherein an amount of the solid catalyst in the reaction zone is in a range from 2 wt. % to 20 wt. %, based on a total amount of the alpha olefin and the vinylidene.

13. The process of claim 1, wherein step (i) and step (ii) are conducted independently at a temperature in a range from 10° C. to 60° C.

14. The process of claim 1, wherein the oligomer product has a weight ratio of trimer:tetramer in a range from 3:1 to 10:1.

15. The process of claim 1, wherein a yield of the oligomer product is at least 2 wt. %, based on a total amount of the alpha olefin and the vinylidene.

16. The process of claim 1, wherein a yield of the oligomer product is from 5 wt. % to 40 wt. %, based on a total amount of the alpha olefin and the vinylidene.

17. The process of claim 1, further comprising a step of separating the solid catalyst from the oligomer product.

18. The process of claim 1, further comprising a step of isolating the oligomer product discharged from the reaction zone.

19. The process of claim 1, further comprising a step of hydrogenating the oligomer product to form a polyalphaolefin.

20. A process comprising:
   (i) contacting an alpha olefin, a vinylidene, and a solid catalyst in a reaction zone, wherein the solid catalyst comprises a solid oxide and/or a chemically-treated solid oxide and the vinylidene comprises a dimer of 1-butene, a dimer of 1-pentene, a dimer of 1-hexene, a dimer of 1-octene, a dimer of 1-decene, a dimer of 1-dodecene, a dimer of 1-tetradecene, a dimer of 1-hexadecene, or any combination thereof; and
   (ii) forming an oligomer product in the reaction zone having a trimer:tetramer weight ratio of at least 2:1.

21. The process of claim 20, wherein the vinylidene comprises a dimer of 1-decene.

22. The process of claim 20, wherein the solid catalyst comprises the solid oxide, and the solid oxide comprises silica-coated alumina.

23. The process of claim 20, wherein the solid catalyst comprises the chemically-treated solid oxide, and the chemically-treated solid oxide comprises sulfated alumina and/or fluorided silica-coated alumina.

24. The process of claim 20, wherein the alpha olefin comprises 1-butene, 1-pentene, 1-hexene, 1-octene, 1-decene, 1-dodecene, 1-tetradecene, 1-hexadecene, or any combination thereof.

25. The process of claim 20, wherein the alpha olefin comprises 1-decene.

26. The process of claim 20, wherein a molar ratio of the alpha olefin to the vinylidene is in a range from 2:1 to 1:2.

27. The process of claim 20, wherein the oligomer product has a weight ratio of trimer:tetramer in a range from 3:1 to 10:1.

28. The process of claim 20, further comprising:
a step of separating the solid catalyst from the oligomer product;
a step of isolating the oligomer product discharged from the reaction zone; and
a step of hydrogenating the oligomer product to form a polyalphaolefin.

29. A process comprising:
(i) contacting an alpha olefin, a vinylidene, and a solid catalyst in a reaction zone, wherein the solid catalyst comprises a solid oxide and/or a chemically-treated solid oxide and an amount of the solid catalyst in the reaction zone is in a range from 2 wt. % to 20 wt. %, based on a total amount of the alpha olefin and the vinylidene; and
(ii) forming an oligomer product in the reaction zone having a trimer:tetramer weight ratio of at least 2:1.

30. The process of claim 29, wherein the solid catalyst comprises the solid oxide, and the solid oxide comprises silica-coated alumina.

31. The process of claim 29, wherein the solid catalyst comprises the chemically-treated solid oxide, and the chemically-treated solid oxide comprises sulfated alumina and/or fluorided silica-coated alumina.

32. The process of claim 29, wherein:
the alpha olefin comprises 1-butene, 1-pentene, 1-hexene, 1-octene, 1-decene, 1-dodecene, 1-tetradecene, 1-hexadecene, or any combination thereof; and
the vinylidene comprises a dimer of 1-butene, a dimer of 1-pentene, a dimer of 1-hexene, a dimer of 1-octene, a dimer of 1-decene, a dimer of 1-dodecene, a dimer of 1-tetradecene, a dimer of 1-hexadecene, or any combination thereof.

33. The process of claim 29, wherein:
the alpha olefin comprises 1-decene; and
the vinylidene comprises a dimer of 1-decene.

34. The process of claim 29, wherein a molar ratio of the alpha olefin to the vinylidene is in a range from 2:1 to 1:2.

35. The process of claim 29, further comprising:
a step of separating the solid catalyst from the oligomer product;
a step of isolating the oligomer product discharged from the reaction zone; and
a step of hydrogenating the oligomer product to form a polyalphaolefin.

* * * * *